(12) United States Patent
Okada et al.

(10) Patent No.: US 8,911,354 B2
(45) Date of Patent: Dec. 16, 2014

(54) RESIN TUBE AND ENDOSCOPE

(71) Applicant: Olympus Medical Systems Corp., Tokyo (JP)

(72) Inventors: Hiromitsu Okada, Hachioji (JP); Mamoru Machiya, Hachioji (JP); Kei Kobayashi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/846,294

(22) Filed: Mar. 18, 2013

(65) Prior Publication Data
US 2013/0253268 A1   Sep. 26, 2013

Related U.S. Application Data

(63) Continuation of application No. PCT/JP2012/072433, filed on Sep. 4, 2012.

(30) Foreign Application Priority Data

Dec. 16, 2011   (JP) ................................. 2011-276370

(51) Int. Cl.
| | | |
|---|---|---|
| *A61B 1/00* | (2006.01) | |
| *A61B 1/04* | (2006.01) | |
| *A61B 1/018* | (2006.01) | |
| *G02B 23/24* | (2006.01) | |
| *A61B 1/005* | (2006.01) | |
| *A61B 1/07* | (2006.01) | |
| *A61B 1/12* | (2006.01) | |
| *A61B 1/012* | (2006.01) | |

(52) U.S. Cl.
CPC .............. *A61B 1/018* (2013.01); *A61B 1/00073* (2013.01); *A61B 1/00137* (2013.01); *G02B 23/2476* (2013.01); *A61B 1/00066* (2013.01); *A61B 1/00094* (2013.01); *A61B 1/00119* (2013.01); *A61B 1/005* (2013.01); *A61B 1/07* (2013.01); *A61B 1/12* (2013.01); *A61B 1/0125* (2013.01); *G02B 23/2423* (2013.01); *G02B 23/2469* (2013.01)
USPC ............ 600/104; 600/132; 600/139; 600/153

(58) Field of Classification Search
USPC .......... 600/102, 104, 123, 128, 132, 139, 153
See application file for complete search history.

(56) References Cited

U.S. PATENT DOCUMENTS

| | | | | |
|---|---|---|---|---|
| 5,735,793 | A | * | 4/1998 | Takahashi et al. ............ 600/153 |
| 5,873,866 | A | * | 2/1999 | Kondo et al. ................. 604/526 |

(Continued)

FOREIGN PATENT DOCUMENTS

| | | |
|---|---|---|
| JP | 05-130971 | 5/1993 |
| JP | 5-46723 | 12/1993 |

(Continued)

OTHER PUBLICATIONS

English Language Abstract Only of JP 06-041701 corresponding to JP 2556002.

(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

A channel tube inserted into an insertion portion of an endoscope includes: a rear side tube including, on a part of an outer surface thereof, a helical-shaped groove; and a front side tube including, on a part of an outer surface thereof, a helical-shaped groove; a connecting pipe for connecting one end of the rear side tube and one end of the front side tube; and a coil wound on the groove of the rear side tube. The rear side tube is connected to the connecting pipe at a part where the groove is formed and the coil is not wound, and the front side tube is connected to the connecting pipe at a part where a coil is not wound.

14 Claims, 15 Drawing Sheets

(56) References Cited

U.S. PATENT DOCUMENTS

| | | | |
|---|---|---|---|
| 2007/0255105 A1* | 11/2007 | Ochi et al. | 600/153 |
| 2007/0282304 A1* | 12/2007 | Ogura et al. | 604/526 |
| 2008/0033239 A1* | 2/2008 | Kogiso | 600/106 |
| 2009/0112066 A1* | 4/2009 | Yago et al. | 600/140 |
| 2009/0234190 A1* | 9/2009 | Sugisawa | 600/140 |
| 2010/0145151 A1* | 6/2010 | Fukunaga et al. | 600/140 |
| 2012/0180896 A1* | 7/2012 | Takahashi | 138/137 |

FOREIGN PATENT DOCUMENTS

| | | |
|---|---|---|
| JP | 2556002 | 8/1997 |
| JP | 2008-229067 | 10/2008 |
| JP | 2009-018070 | 1/2009 |

OTHER PUBLICATIONS

Partial English Translation Only of JP H02-118502 corresponding to JP 5-46723.

\* cited by examiner

RESIN TUBE AND ENDOSCOPE

CROSS REFERENCE TO RELATED APPLICATION

This application is a continuation application of PCT/JP2012/072433 filed on Sep. 4, 2012 and claims benefit of Japanese Application No. 2011-276370 filed in Japan on Dec. 16, 2011, the entire contents of which are incorporated herein by this reference.

BACKGROUND OF THE INVENTION

1. Field of the Invention

The present invention relates to a resin tube and an endoscope, and more particularly to a resin tube configured to be inserted into a flexible tube and the like of an endoscope, and the endoscope.

2. Description of the Related Art

Conventionally, endoscope apparatuses have been widely used in medical fields and industrial fields. Endoscope apparatuses are configured such that an endoscope insertion portion is inserted into an observation target and an image in the observation target is picked up by an image pickup portion provided at a distal end of the insertion portion to display the image on the monitor, thereby enabling a user to view the picked-up image and perform examination and the like in the observation target. Endoscopes include various types, and some endoscopes include inside an endoscope insertion portion a resin tube for a treatment instrument insertion channel or the like.

For example, as disclosed in Japanese Patent Application Laid-Open Publication No. 2008-229067, a resin tube for a treatment instrument insertion channel has one end connected to a treatment instrument insertion port provided to an operation portion and the other end connected to a treatment instrument opening located at a distal end portion of an insertion portion, and a surgeon inserts a treatment instrument from the treatment instrument insertion port to allow the treatment instrument to pass through the resin tube and protrude from the treatment instrument opening, and thereby capable of performing treatment.

In such a case, a coil for preventing buckling and deforming of the resin tube is wound around the resin tube, and the resin tube is inserted through the insertion portion having flexibility. The length of the resin tube is different depending on a length of an insertion portion of each of various types of endoscopes. Therefore, resin tubes are produced by processing such that each of the resin tubes has a length determined for each type of endoscopes.

SUMMARY OF THE INVENTION

A resin tube according to one aspect of the present invention is configured to be inserted in a flexible tube of an endoscope or a connection cable, and the resin tube includes: a first tube including, on a part of an outer surface thereof, a helical-shaped first groove; a second tube including, on a part of an outer surface thereof, a helical-shaped second groove; a connecting pipe configured to connect one end of the first tube and one end of the second tube; a first coil wound on the first groove of the first tube; and a second coil wound on the second groove of the second tube; wherein the first tube is connected to the connecting pipe at a part where the first groove is formed and the first coil is not wound, and the second tube is connected to the connecting pipe at a part where the second coil is not wound.

An endoscope according to one aspect of the present invention comprises: an insertion portion including a flexible tube configured to be inserted into an observation target; an operation portion provided in a linked manner on a proximal end side of the insertion portion; a connection cable configured to connect the operation portion and other devices; and a resin tube configured to be inserted into the flexible tube or the connection cable, the resin tube including: a first tube including, on a part of an outer surface thereof, a helical-shaped first groove; a second tube including, on a part of an outer surface thereof, a helical-shaped second groove; a first coil wound on the first groove of the first tube; a second coil wound on the second groove of the second tube; and a connecting pipe configured to connect one end of the first tube and one end of the second tube, wherein the first tube is connected to the connecting pipe at a part where the first groove is formed and the first coil is not wound, and the second tube is connected to the connecting pipe at a part where the second coil is not wound.

DETAILED DESCRIPTION OF THE PREFERRED EMBODIMENT(S)

Figure 1:
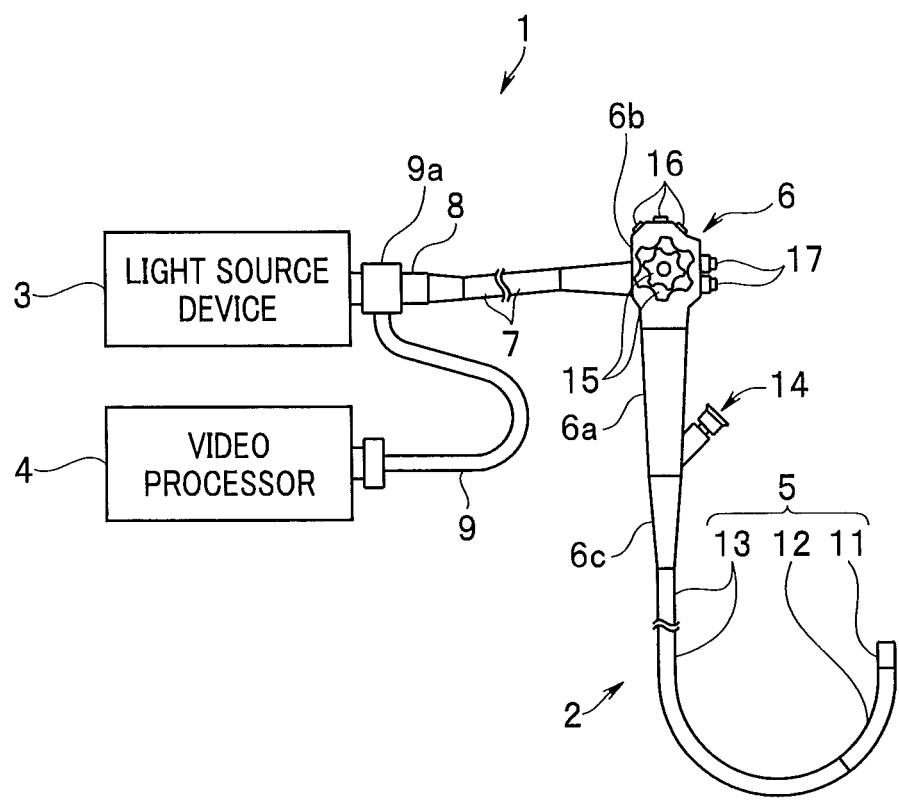
FIG. 1 is a configuration diagram illustrating a configuration of an endoscope apparatus according to a first embodiment of the present invention.

Hereinafter, embodiments of the present invention will be described with reference to drawings.

Note that, in the drawings used for the explanation below, scale sizes are different for each of the constituent elements such that the respective constituent elements have sizes recognizable in the drawings. Therefore, the present invention is not limited only to the number, the shapes, the ratio of the sizes of the constituent elements, and the relative positional relationship among the respective constituent elements shown in the drawings.

First Embodiment (Configuration of Endoscope Apparatus)

FIG. 1 is a configuration diagram showing a configuration of an endoscope apparatus according to the present embodiment. An endoscope apparatus 1 is configured by including an endoscope 2, a light source device 3 that supplies illumination light to the endoscope 2, and a video processor 4 that performs signal processing on an image pickup signal from the endoscope 2. The video processor 4 is connected with a monitor, not shown, and an endoscopic image is displayed on the monitor.

The endoscope 2 includes an insertion portion 5, an operation portion 6 provided in a linked manner on a proximal end side of the insertion portion 5, and a universal cord 7 extended from a side portion of the operation portion 6. A light guide connector 8 detachably connected to the light source device 3 is provided on an end portion of the universal cord 7 which is a connection cable connecting the operation portion and the light source device 3.

A connector 9a for a cable 9 for connecting to the video processor 4 is provided on a side portion of the light guide connector 8. One end of the cable 9 is detachably connected to the connector 9a and the other end of the cable 9 is connected to the video processor 4.

The insertion portion 5 includes in the following order from the distal end side, a rigid distal end portion 11, a bending portion 12, and a flexible tube portion 13 which is long and has flexibility, in a linked manner.

The operation portion 6 includes a grasping portion 6a and an operation portion main body 6b. The grasping portion 6a is a part grasped by a surgeon and has a forceps port 14 as a treatment instrument insertion port. The operation portion main body 6b is provided with two bending operation knobs 15, various kinds of operation switches 16, various buttons 17 such as a suction button and an air/water feeding button, etc. The forceps port 14 is an opening for inserting a forceps, for example, as a treatment instrument.

Figure 3:
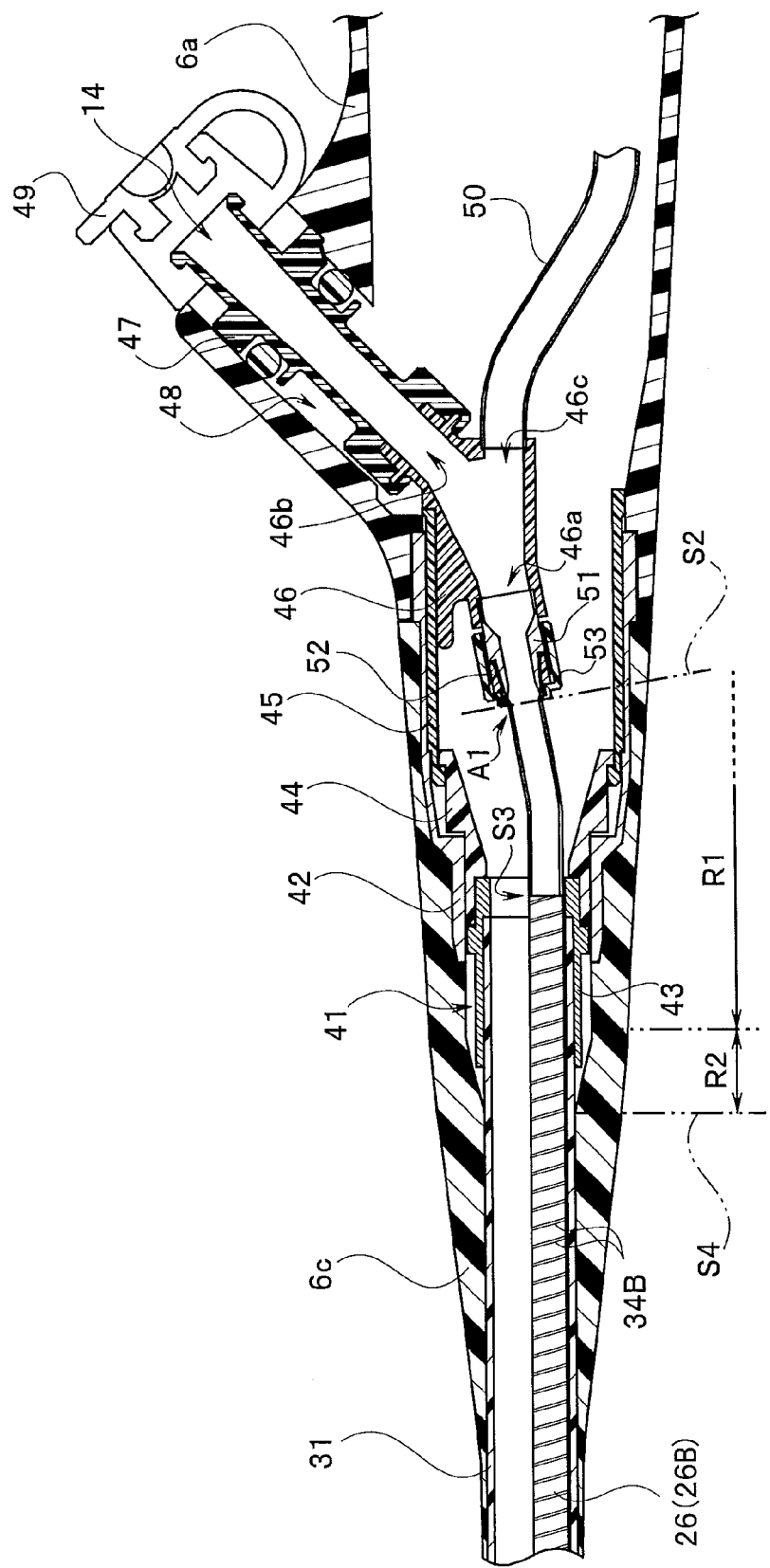
FIG. 3 is a cross-sectional view of a distal end portion of an operation portion 6 according to the first embodiment.

A proximal end portion of the insertion portion 5 is connected to a connecting member 44 shown in FIG. 3 in a break-prevention portion 6c on the distal end side of the operation portion 6.

(Configuration of Endoscope)

Figure 2:
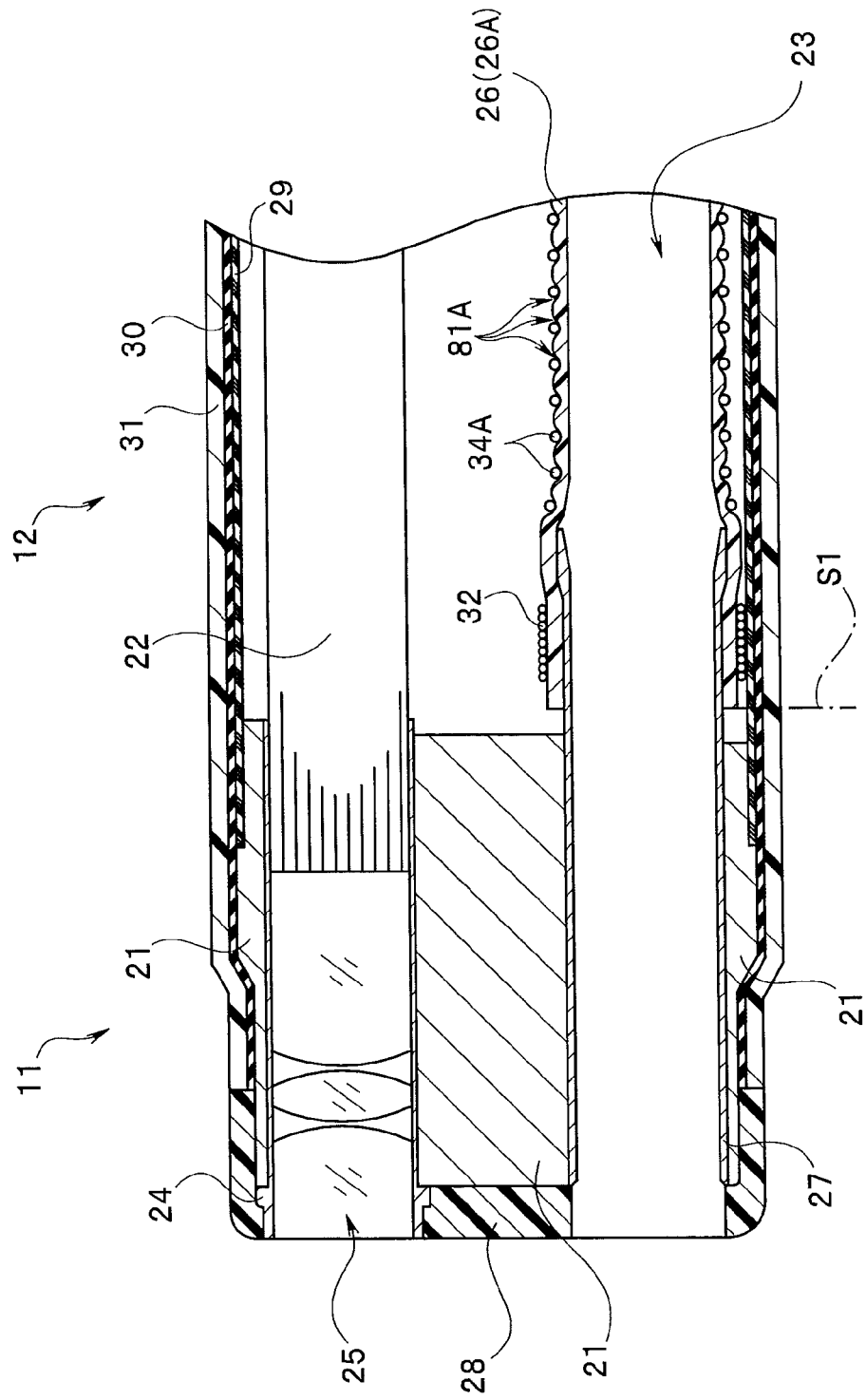
FIG. 2 is a cross-sectional view of a distal end portion 11 of an insertion portion 5 of an endoscope 2 according to the first embodiment.

FIG. 2 is a cross-sectional view of the distal end portion 11 of the insertion portion 5 of the endoscope 2. The distal end portion 11 has a rigid distal end portion main body 21. The distal end portion main body 21 includes a plurality of holes from which an image pickup unit, a light guide, and the like are incorporated. FIG. 2 shows a cross section of the distal end portion 11 along an axis direction of the insertion portion 5, and only two holes for a light guide 22 and a treatment instrument insertion channel 23 are shown in FIG. 2.

A distal end portion of the light guide 22 composed of a plurality of optical fibers are inserted into a proximal end portion of a pipe 24 made of metal to be connected thereto. An illumination optical system 25 configured by a plurality of lenses is attached to the inside of the distal end side of the pipe 24. The illumination light from the light source device 3 is emitted from the distal end portion of the light guide 22, to be irradiated to a subject through the illumination optical system 25.

A metal pipe 27 to which the channel tube 26 for treatment instrument insertion channel as a resin tube is connected is internally fitted in the hole for treatment instrument insertion channel 23 and fixed thereto. The channel tube 26 is a resin tube inserted into the insertion portion 5 as a flexible tube of the endoscope 2. Note that, as described later, the channel tube 26 is composed of a front side tube 26A and a rear side tube 26B, and the front side tube 26A is arranged on the distal end portion 11 side of the insertion portion 5. A proximal end portion of the pipe 27 has a diameter expanded along the proximal end direction, and the channel tube 26 is externally fitted to the proximal end portion of the pipe 27 and connected thereto. An image pickup unit and the like, not shown, are also attached to the distal end portion main body 21. An insulating cover 28 is fitted on the distal end surface of the distal end portion 11 of the insertion portion 5 so as to cover the distal end surface.

A distal end bending piece of the bending portion 12 having a plurality of bending pieces 29 is fixed at the proximal end portion of the distal end portion main body 21. In addition, a braid 30 is provided from the proximal end of the cover 28 toward the proximal end portion of the insertion portion 5 so as to cover the distal end portion main body 21 and a plurality of bending pieces 29. Furthermore, an outer cover 31 is provided on the outer circumference of the braid 30.

The distal end portion of the front side tube 26A of the channel tube 26 is connected to the proximal end portion of the pipe 27, and the distal end portion of the front side tube 26A around which a thread 32 is wound is further fixed to the pipe 27 with adhesive (not shown).

Although a coil 34A is wound around the outer surface of the front side tube 26A at a predetermined pitch, the coil 34A is not wound around the distal end portion of the front side tube 26A. The front side tube 26A is connected to the pipe 27 such that the part of the front side tube 26A where the coil 34A is not wound covers the pipe 27 when the distal end portion of the front side tube 26A is externally fitted to the proximal end portion of the pipe 27. At that time, the distal end of the front side tube 26A is located at a position S1 in FIG. 2.

FIG. 3 is a cross-sectional view of the distal end portion of the operation portion 6. The break-prevention portion 6c having a diameter which becomes smaller toward the distal end is provided on the proximal end side of the grasping portion 6a. The break-prevention portion 6c and the grasping portion 6a are made of resin. The break-prevention portion 6c has a cylindrical shape which becomes thinner toward the distal end. The break-prevention portion 6c has a region (rigid portion) R1 where the rear side tube 26B as the resin tube arranged inside is completely unbendable and a region (quasi-rigid portion) R2 where the rear side tube 26B is hardly bendable. The region (rigid portion) R1 where the rear side tube 26B is completely unbendable and the region (quasi-rigid portion) R2 where the rear side tube 26B is hardly bendable are determined depending on the structure of the operation portion 6.

A hole 41 through which the proximal end portion of the insertion portion 5 is inserted is formed in the break-prevention portion 6c. The hole 41 has a part, inner diameter of which gradually becomes larger toward the proximal end side, and a cylindrical fixing member 42 is mounted onto and fixed to the hole 41 so as to be fitted thereon. The fixing member 42 includes a plurality of step portions made of metal, and a flexible tube ferrule 43 connected to the proximal end portion of the flexible tube portion 13 is internally fitted to the distal end portion of the fixing member 42 and fixed thereto.

A forceps channel bifurcation portion 46 is connected to the proximal end portion of the flexible tube ferrule 43 through two connecting members 44, 45. The two connecting members 44, 45 are fixed to the hole 41 located inside the fixing member 42 so as to be fitted to the hole. The forceps channel bifurcation portion 46 is connected to the proximal end portion of the connecting member 45. Furthermore, at the proximal end portion of the forceps channel bifurcation portion 46, a forceps port member 47 having the forceps port 14 is connected and fixed. The forceps port member 47 is internally fitted and fixed to a hole 48 formed at the grasping portion 6a. A cap 49 is attached to the forceps port 14 of the forceps port member 47.

The forceps channel bifurcation portion 46 has, on the distal end side thereof, a connection opening 46a to which the proximal end portion of the rear side tube 26B is connected, and has, on the proximal end side thereof, a connection opening 46b communicating with the forceps port 14, and a connection opening 46c to be connected with a tube 50 for suctioning, for example.

As shown in FIG. 3, a connecting member 51 having a screw portion on the outer circumferential portion thereof is fixed to the connection opening 46a. A tapered tube 52 is provided on the outer circumferential portion of the connecting member 51 in a loose manner. A clamp nut 53 is provided on the outer circumferential portions of the connecting member 51 and the tapered tube 52, and a screwing position between the screw portion of the connecting member 51 and a screw portion formed on the inner circumferential surface of the clamp nut 53 is changed by rotating the clamp nut 53.

When the clamp nut 53 is rotated to be moved toward the distal end side, a gap is generated between the connecting member 51 and a tapered surface of the tapered tube 52. Alternatively, when the clamp nut 53 is rotated in the reverse direction to be moved toward the proximal end side, the gap between the connecting member 51 and the tapered surface of the tapered tube 52 becomes small. Therefore, when the proximal end portion of the rear side tube 26B is inserted into the gap between the connecting member 51 and the tapered surface of the tapered tube 52 with the clamp nut 53 being positioned on the distal end side, and thereafter the clamp nut 53 is rotated in the reverse direction to move the clamp nut toward the proximal end side, the proximal end portion of the rear side tube 26B is sandwiched between the connecting member 51 and the tapered surface of the tapered tube 52 to be fixed to the forceps channel bifurcation portion 46.

Note that a part of the proximal end portion of the rear side tube 26B, which is located in the vicinity of the clamp nut 53, may be covered with a heat-shrinkable tube for buckling prevention.

In the present embodiment, the above-described completely unbendable region R1 is a range from the halfway portion of the proximal end portion of the flexible tube ferrule 43 toward the operation portion main body 6a side, and the hardly bendable region R2 is a range from the halfway portion of the proximal end portion of the flexible tube ferrule 43 toward the distal end side to the position at which the inner diameter of the hole 41 expands toward the proximal end side.

In FIG. 3, the coil 34B is not wound around the area in the vicinity of the position S2 at which the proximal end portion of the rear side tube 26B is fixed, but the coil 34B is wound around the area on the more distal end side than the position S2. In order to prevent the rear side tube 26B from buckling at the coil end when the insertion portion 5 is bent, a position S3 of the coil end of the coil 34B is located within a range from the region (rigid portion) R1 in which the resin tube 26 inside the operation portion 6 of the endoscope 2 is completely unbendable to the region (quasi-rigid portion) R2 in which the resin tube is hardly bendable.

That is, as shown in FIG. 3, the coil 34B is not wound around the area from the position S2 to the position S3 on the proximal end side of the rear side tube 26B, but wound around the area which is more distal end side than the position S3. The position S3 is located in a range from the position S2 at which the proximal end portion of the rear side tube 26B is fixed to the position S4 which is the distal end portion of the region (quasi-rigid portion) R2 in which the rear side tube 26B is hardly bendable.

(Configuration of Channel Tube)

Figure 7:
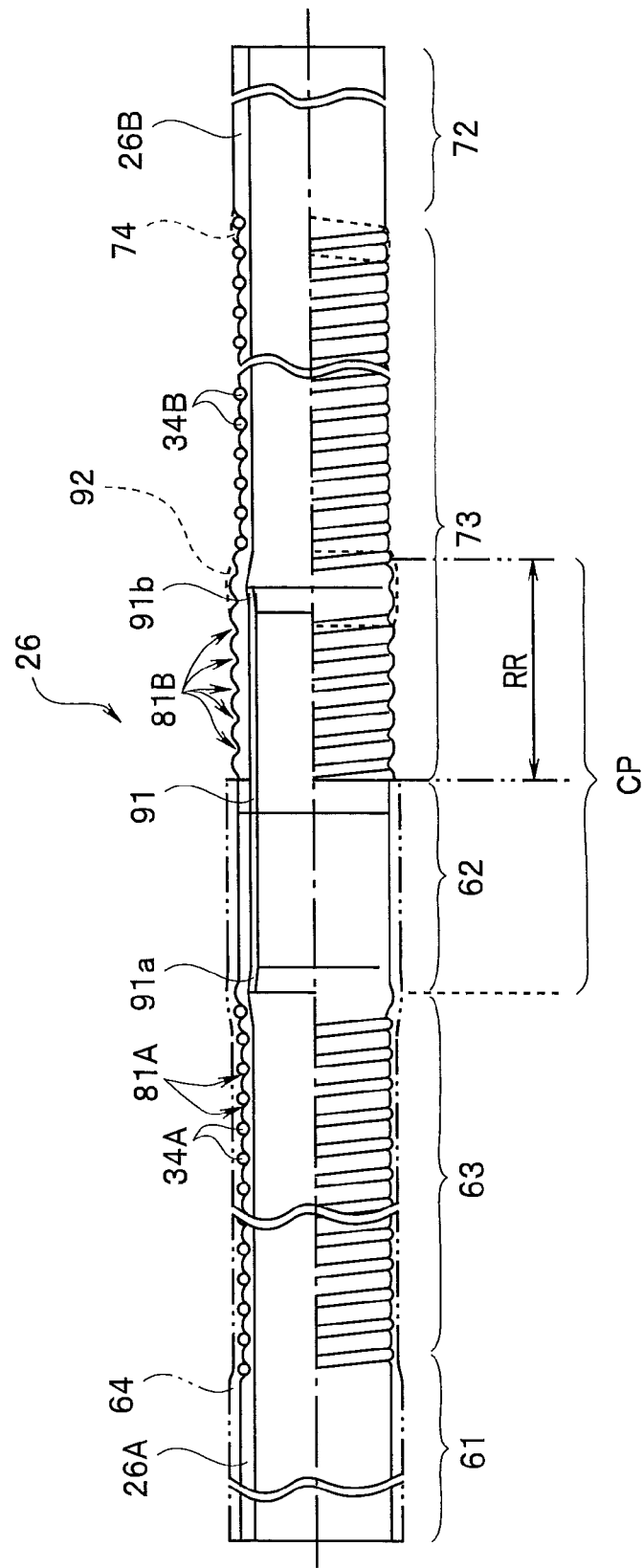
FIG. 7 relates to the first embodiment, and is an exterior view of a channel tube 26 in a state where the front side tube 26A and the rear side tube 26B are connected to each other with the connecting pipe 91.

Next, the configuration of the above-described channel tube 26 inserted through the insertion portion 5 will be described. In the present embodiment, the channel tube 26 is configured by connecting two members. One of the two members is the front side tube 26A, and the other is the rear side tube 26B. The front side tube 26A and the rear side tube 26B are connected to each other with the connecting pipe 91 (FIG. 7).

First, description will be made on the configurations of the front side tube 26A and the rear side tube 26B in a state before the front side tube and the rear side tube are connected to each other with the connecting pipe 91.

Figure 4:
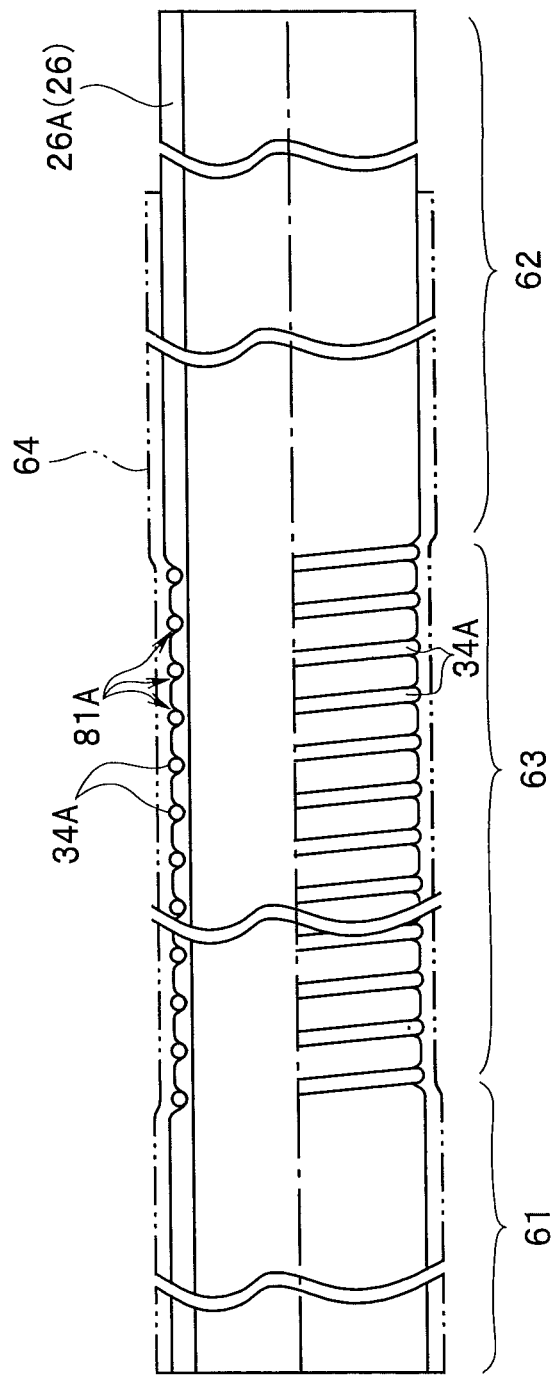
FIG. 4 relates to the first embodiment, and is an exterior view illustrating a configuration of a front side tube 26A in a state before being connected using a connecting pipe.

FIG. 4 is an exterior view illustrating the configuration of the front side tube 26A in a state before being connected using the connecting pipe 91. The front side tube 26A has a tube main body around which the coil 34A is wound. The front side tube 26A has, at both end portions thereof, parts around which the coil 34A is not wound. As shown in FIG. 4, a coil winding portion 63 around which the coil 34A is wound is located between a coil non-winding portion 61 around which the coil 34A is not wound on the distal end side and a coil non-winding portion 62 around which the coil 34A is not wound on the proximal end side. The surfaces of the coil non-winding portions 61 and 62 are smooth surfaces without a groove.

A helical-shaped groove 81A having a predetermined depth is formed on the coil winding portion 63 on the surface of the tube main body of the front side tube 26A, and the coil 34A is wound along the groove 81A. That is, the front side tube 26A is a tube having, on a part of the outer surface thereof, the helical-shaped groove 81A, and the coil 34A is wound on the groove 81A of the front side tube 26A.

Furthermore, as shown by the two-dot chain lines in FIG. 4, a coating layer 64 formed by resin such as polyurethane being applied as a coating material is provided on the surface of the front side tube 26A around which the coil 34A is wound. The resin coating is applied in order to prevent the coil 34A from floating from the surface of the tube main body or prevent the position of the coil 34A from shifting on the surface of the tube main body, when the insertion portion 5 is bent.

In addition, although both of the front side tube 26A and the rear side tube 26B have elasticity, the front side tube 26A has a larger elasticity than the rear side tube 26B, since the front side tube has the coating layer 64. Note that the rigidities or elasticities of the front side tube 26A and the rear side tube 26B can be made different from each other by the presence and absence of the coating layer. However, when both of the front side tube 26A and the rear side tube 26B are coated, the rigidities or elasticities of the front side tube 26A and the rear side tube 26B can be made different from each other by changing the kind or thickness of the coating material, or the range in which the coating material is applied, for each of the tubes. Therefore, both of or at least one of the front side tube 26A and the rear side tube 26B may be coated.

Figure 5:
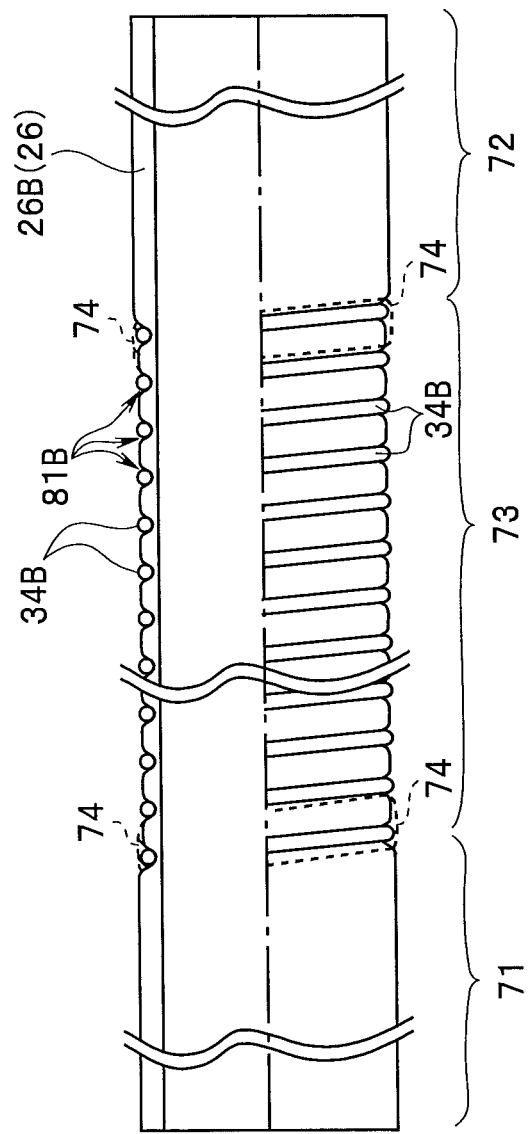
FIG. 5 relates to the first embodiment, and is an exterior view illustrating a configuration of a rear side tube 26B in a state before being connected using the connecting pipe.

FIG. 5 is an exterior view illustrating a configuration of a rear side tube 26B in a state before being connected using the connecting pipe. The rear side tube 26B has a tube main body around which the coil 34B is wound. The rear side tube 26B has, at both end sides thereof, parts around which the coil 34B is not wound. As shown in FIG. 5, a coil winding portion 73 around which the coil 34B is wound is located between a coil non-winding portion 71 around which the coil 34B is not wound on the distal end side and a coil non-winding portion 72 around which the coil 34B is not wound on the proximal end side. The surfaces of the coil non-winding portions 71 and 72 are smooth surfaces without a groove.

A helical-shaped groove 81B having a predetermined depth is formed on the coil winding portion 73 on the surface of the tube main body of the rear side tube 26B, and the coil 34B is wound along the groove 81B. That is, the rear side tube 26B is a tube having, on a part of the outer surface thereof, the helical-shaped groove 81B, and the coil 34B is wound on the groove 81B of the rear side tube 26B. In addition, the coil 34B has, at the distal end portion and the rear end portion thereof, a resin-applied portion 74 formed by an epoxy resin or the like being applied.

Note that, as described later, since the distal end side part of the rear side tube 26B is peeled and removed for adjusting the length of the rear side tube 26B, the distal end side coil non-winding portion 71 around which the coil 34B is not wound is not necessarily provided.

Each of the tube main bodies of the front side tube 26A and the rear side tube 26B has an outer diameter of 3 mm to 5 mm, and a thickness of 0.3 mm to 0.5 mm, and is made of a resin material such as PTFE (polytetrafluoroethylene), for example. Both of or at least one of the wires configuring the coils 34A and 34B has a spring property, and the cross-sectional shape of the wires is a circular shape, for example. In this case, the wires of the coils do not have edge portions such as corner portions of a quadrangle, which gives no damage on other internal components.

Each of the coils 34A and 34B is configured by a metal wire made of a metal material such as stainless steel, and the diameter of each of the wires is 0.2 mm to 0.3 mm, for example. Note that each of the coils 34A and 34B may be configured by a resin wire made of resin. In addition, both of the coils 34A and 34B do not have to have a spring property.

Figure 6:
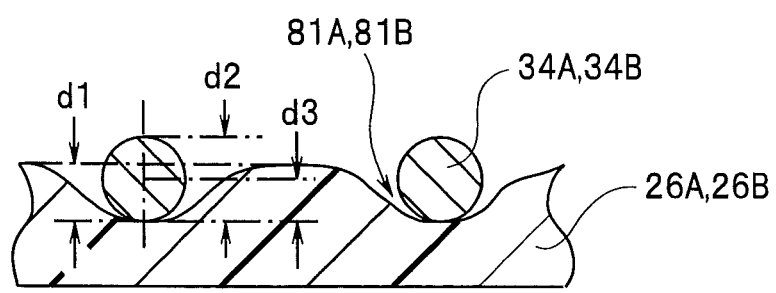
FIG. 6 relates to the first embodiment, and is a partial cross-sectional view for illustrating surface states of tube main bodies around which coils 34A and 34B are wound, respectively.

FIG. 6 is a partial cross-sectional view for illustrating surface states of tube main bodies around which the coils 34A and 34B are wound, respectively. As shown in FIG. 6, the front side tube 26A and the rear side tube 26B have on the surfaces thereof the groove 81A and the groove 81B formed previously at the parts around which the coil 34A and the coil 34B are wound, respectively. The coils 34A and the coil 34B are wound around the surfaces of the front side tube 26A and the rear side tube 26B so as to get in the groove 81A and the groove 81B, respectively.

Each of the grooves 81A and 81B has a depth d1 which is smaller than a diameter d2 of the wire of each of the coils 34A and 34B, and larger than a radius d3 of the wire of each of the coils. Therefore, each of the wires gets in each of the grooves 81A and 81B by the dimension of more than half of the diameter d2. As a result, an irregularities created by the coils protruded from the surface of the channel tube 26 are small.

When another internal component around the channel tube 26 moves in the axis direction of the insertion portion 5 and contacts the coils 34A and 34B due to the bending of the insertion portion 5, etc., even if the coils 34A and 34B bump into a projected portion of the other internal component, the projected portion of the other internal component slides on the surfaces of the coils 34A and 34B, since the irregularities created by the coils are small. Therefore, the channel tube 26 does not interfere with the movement of the other internal components. In addition, since the irregularities created by the coils are small, the surface of the coating layer 64 formed by the coating material is also smooth.

Note that the coil 34A wound around the front side tube 26A and the coil 34B wound around the rear side tube 26B may differ from each other in at least one of rigidities and elasticities.

Furthermore, the rigidities or elasticities of the front side tube 26A and the rear side tube 26B can be made different from each other by setting at least one of the diameters of the wires of the coils 34A and 34B, the materials of the wires of the coils, the helical pitches of the respective coils, and the depths of the grooves so as to be different from each other.

FIG. 7 is an exterior view of the channel tube 26 in a state where the front side tube 26A and the rear side tube 26B are connected to each other with the connecting pipe 91. The channel tube 26 is configured by joining the front side tube 26A and the rear side tube 26B with the connecting pipe 91. The connecting pipe 91 is a rigid member for connecting one end of the front side tube 26A and one end of the rear side tube.

The connecting pipe 91 is a cylindrical member made of metal such as stainless steel, and has at both end portions diameter-expanded portions 91a, 91b. The front side tube 26A and the rear side tube 26B are externally fitted respectively to the both end portions of the connecting pipe 91 and connected thereto, and the respective tubes are surely connected and fixed to the connecting pipe 91 with the diameter-expanded portions 91a, 91b. A part of the channel tube 26, which is located around the connecting pipe 91, serves as a coupling portion CP. That is, the coupling portion CP is the part covering the connecting pipe 91 of the channel tube 26.

The coil non-winding portion 62 of the front side tube 26A is connected to the distal end side of the connecting pipe 91 so as to be externally fitted thereto. That is, the front side tube 26A is connected to the connecting pipe 91 at the part where the coil 34A is not wound.

In order to obtain the channel tube 26 having a desired length, the rear side tube 26B is cut at the halfway portion of the coil winding portion 73, and the coil 34B wound around the region RR in the range externally fitted to the connecting pipe 91 is peeled. The rear side tube 26B is connected to the connecting pipe 91 such that the coil removed region RR, where the coil 34B wound around the coil winding portion 73 is peeled and removed, covers the connecting pipe 91. Therefore, only the groove 81B exists on the outer surface of the coil winding portion 73 in the coil removed region RR which covers the connecting pipe 91. That is, the rear side tube 26B is connected to the connecting pipe 91 at the region RR where the groove 81B is formed and the coil 34B is not wound.

Then, a resin material 92 such as an epoxy resin is applied to a part of the rear side tube 26B, the part being around the proximal end side of the connecting pipe 91. In other words, the end portion of the coil 34B wound around the rear side tube 26B, the end portion being located on the connecting pipe 91 side, is covered with the resin material 92.

The resin material 92 is applied so as to cover the coil end on the distal end side of the rear side tube 26B. Since the coil end of the coil 34B is cut, the resin material is applied in order to prevent the coil end from detaching from the rear side tube 26B and prevent other internal components around the edge of the cut portion from being damaged by the edge of the cut portion, and furthermore, in order not to cause a great change in rigidity at the border between the coil end and the part where the coil is removed.

As described above, the front side tube 26A is subjected to resin coating and the rear side tube 26B is not subjected to resin coating, the rigidities of the front side tube 26A and the rear side tube 26B are different from each other. That is, the rigidity of the front side tube 26A is higher than that of the rear side tube 26B. Therefore, the front side tube is less likely to bend than the rear side tube.

Note that the rigidities of the front side tube 26A and the rear side tube 26B may be made different from each other by the difference in the helical pitches of the grooves 81A and that of 81B, or by the difference in the diameters, materials, or the like of the wires of the coils 34A and 34B.

Note that the proximal end portion of the front side tube 26A and the distal end portion of the rear side tube 26B, which are externally fitted to the connecting pipe 91, closely adhere to each other in FIG. 7. However, the front side tube 26A and the rear side tube 26B may be connected to the connecting pipe 91 such that a predetermined gap is generated between the proximal end portion of the front side tube 26A and the distal end portion of the rear side tube 26B.

Furthermore, as described later, the front side tube 26A is used without being cut. Therefore, the coil 34A does not have to be wound around the front side tube 26A. In such a case, a tube having bending resistance, toughness, or the like is used as the front side tube 26A. Such a tube includes a tube made of ePTFE (expanded PTFE) having a porous structure, for example. Japanese Patent Application Laid-Open Publication No. 7-1630 discloses an art related to a tube made of ePTFE having a porous structure, for example.

Figure 8:
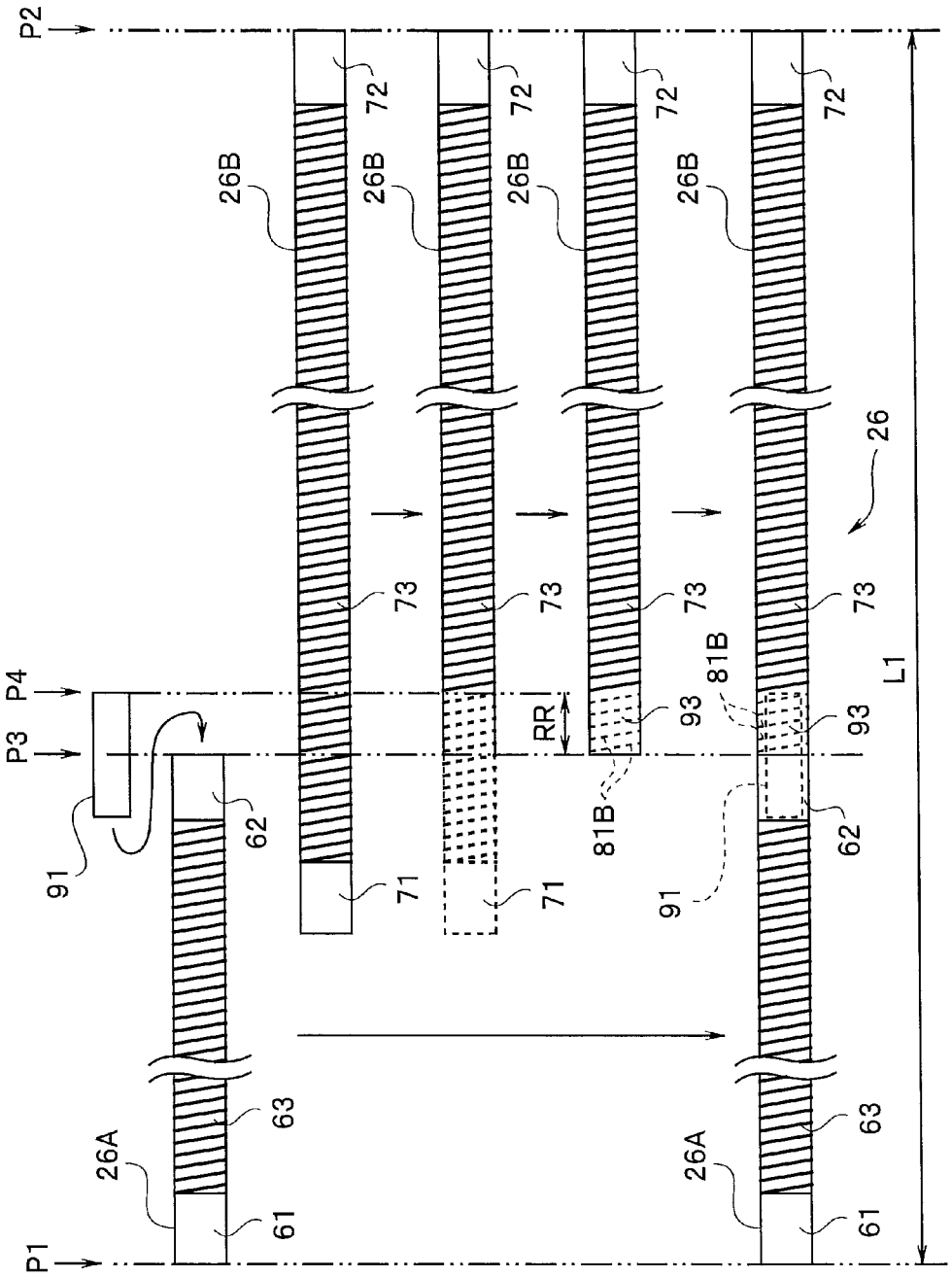
FIG. 8 relates to the first embodiment, and illustrates an example of a method of producing a channel tube 26 by processing the channel tube into a desired length by connecting the front side tube 26A and the rear side tube 26B to each other with the connecting pipe.

FIG. 8 illustrates an example of a method of producing the channel tube 26 by processing the channel tube into a desired length by connecting the front side tube 26A and the rear side tube 26B to each other with the connecting pipe.

The front side tube 26A and the rear side tube 26B, and the connecting pipe 91, which have been described with reference to FIG. 4 and FIG. 5, are prepared in advance. High processing accuracy is not required for each of the lengths of the front side tube 26A and the rear side tube 26B.

When the channel tube 26 having a length L1 is produced, for example, the proximal end portion of the front side tube 26A is connected as-is to the connecting pipe 91. That is, the coil non-winding portion 62 of the front side tube 26A is externally fitted and connected to the distal end side of the connecting pipe 91.

For example, by using a jig having a length L1, the distal end of the front side tube 26A is placed at the position of one end portion P1 of the length L1 of the jig. The length L1 is determined in accordance with the length between the reference S1 in FIG. 2 and the reference S2 in FIG. 3, and the entire length L1 of the tube 26 is determined by including the clamping margin in the connection using the clamp nut 53.

On the other hand, the proximal end of the rear side tube 26B is placed at the position of the other end portion P2 of the length L1 of the jig, and the position P3 of the rear side tube 26B at the time that the rear side tube is connected to the connecting pipe 91 which is connected to the front side tube 26A is determined. A part of the coil 34B, which is located in the range from the position P3 to the position P4 which is the position of the proximal end of the connecting pipe 91 when the rear side tube 26B is externally fitted and connected to the connecting pipe 91, is peeled, cut, and removed.

The rearside tube 26B from which the distal end side of the coil 34B is removed is cut at the position P3. A coil-removed portion 93 in the region RR where the rear side tube is cut at the position P3 and the coil 34B is removed is the part where the groove 81B is formed.

The coil 34B is not wound around the coil-removed portion 93. Therefore, the rear side tube 26B can be connected to the connecting pipe 91 so as to be externally fitted thereto.

After that, though not shown in FIG. 8, the resin material 92 shown in FIG. 7 is applied to a part of the rear side tube 26B, the part being around the proximal end of the connecting pipe 91.

As described above, in order to obtain the channel tube 26 having a necessary length L1 when the front side tube 26A is used as-is, and the front side tube 26A and the rear side tube 26B are connected to each other with the connecting pipe 91, the distal end portion of the coil 34B on the rear side tube 26B is removed, the distal end portion of the rear side tube 26B is cut, and the coil-removed portion 93 of the rear side tube 26B is connected to the connecting pipe 91.

As a result, the channel tube 26 formed by connecting the front side tube 26A and the rear side tube 26B with the connecting pipe 91 can be formed into the desired length L1.

If the channel tube 26 is attempted to be formed by one tube member as in conventional tubes, since the tube is made of a thin and soft material, it has not been easy to produce the channel tube by processing the tube member around which the coil is wound into a desired length with high accuracy. However, as described above, the channel tube 26 is configured by the two tubes, and one of the tubes is connected to the connecting member 91 after the length of the one of the tubes is adjusted and the coil 34B which is located on a part of the one of the tubes is peeled, the part of the one of the tubes being externally fitted and connected to the connecting coil 91 as the connecting member. Therefore, even if the processing accuracy of the lengths of the two tubes is not high, it is possible to easily produce the channel tube 26 having a desired length with high accuracy.

In addition, the coupling portion CP at which the two tubes 26A and 26B are connected with the connecting pipe 91 has a part having the largest outer diameter of the channel tube 26. Also other internal components are inserted in the insertion portion 5. Therefore, it is preferable to place the coupling portion CP in a region which does not interfere with diameter changing positions of the other internal components such that the movements of the other internal components are never impeded by the coupling portion contacting the other internal components.

Figure 9:
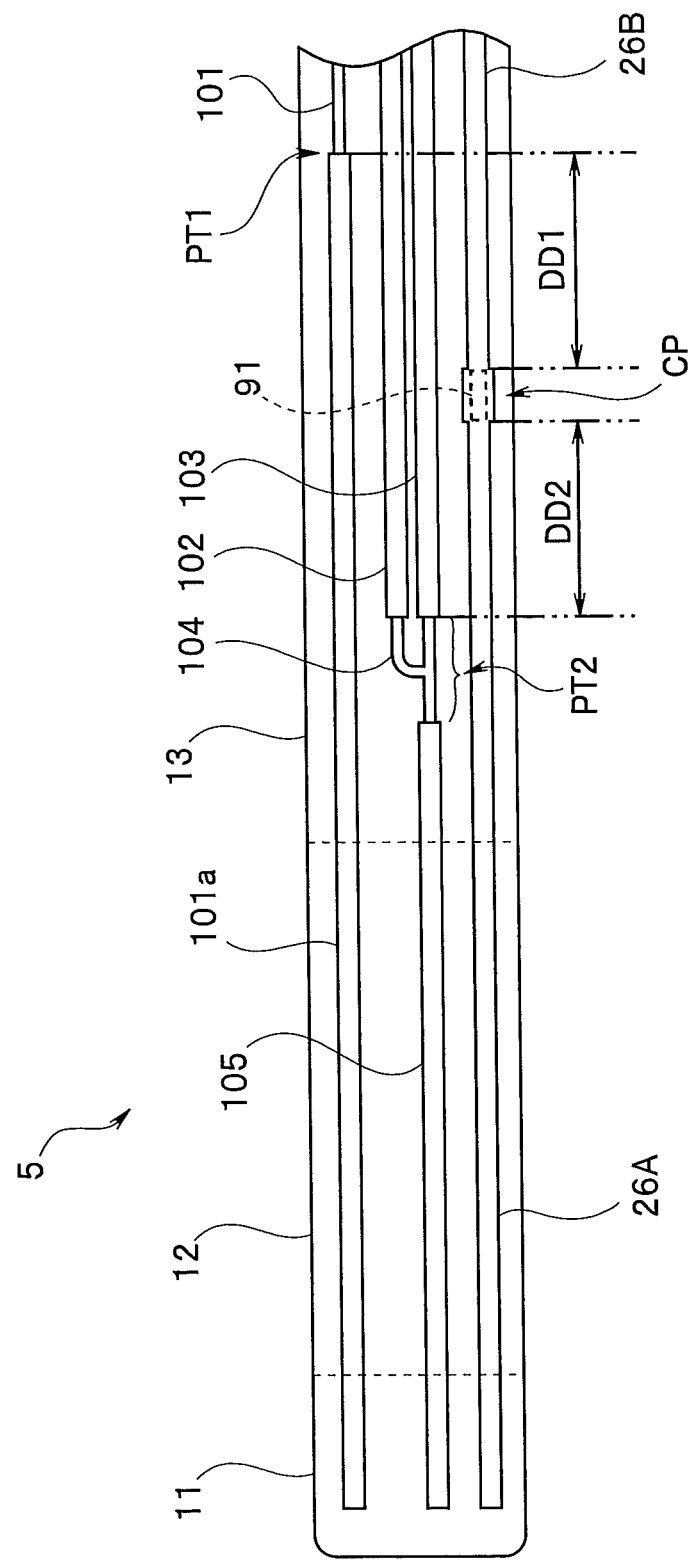
FIG. 9 relates to the first embodiment, and illustrates a positional relationship between the channel tube 26 and other internal components.

FIG. 9 illustrates a positional relationship between the channel tube 26 and other internal components. In addition to the channel tube 26, various internal components are inserted through the insertion portion 5. However, FIG. 9 illustrates, as the internal components, only a light guide 101 for illumination, a water-feeding channel tube 102, an air-feeding channel tube 103, an air-feeding/water-feeding channel bifurcating member 104, and an air-feeding/water-feeding channel tube 105. Other than these internal components, a bending wire and the like are inserted. However, such components are omitted in FIG. 9.

The light guide 101 has a part covered with a protection member 101a for light guide protection, and a diameter changing point PT1 at which the diameter of the light guide 101 changes exists at the end portion of the protection member 101a. In addition, the air-feeding/water-feeding channel bifurcating member 104 connects the water-feeding channel tube 102 and the air-feeding channel tube 103 with the air-feeding/water-feeding channel tube 105, and a diameter changing point PT2 exists at a position or in a region where the air-feeding/water-feeding channel bifurcating member 104 is located.

The length of the front side tube 26A is set such that these diameter changing points PT1, PT2 and the coupling portion CP of the channel tube 26 do not contact each other in a state where the insertion portion 5 is straight, and further in any bending state of the insertion portion 5. That is, the connecting pipe 91 is disposed at a position different from the diameter changing points of the other internal components in the insertion portion 5, in the axis direction of the insertion portion 5 as a flexible tube.

As shown in FIG. 9, the length of the front side tube 26A is set also in view of the production error of the front side tube 26A such that the coupling portion CP is located at a position away from the diameter changing point PT1 by a distance DD1 and away from the diameter changing point PT2 by a distance DD2 in the state where the insertion portion 5 is straight. The distance DD1 and the distance DD2 are distances set for preventing the diameter changing points PT1, PT2 from being interfered with by the coupling portion CP even when the insertion portion 5 is bent to maximum in up, down, left and right directions.

The distances DD1, DD2 are calculated and determined based on a moving range of the diameter changing points of the other internal components with respect to the coupling portion CP in the axis direction of the insertion portion 5, the moving range being due to a difference in inner circumferences generated when the insertion portion 5 is bent in the maximum bending range in the four directions, i.e., up, down, left and right directions. The distances DD1, DD2 are thus determined, which prevents the coupling portion CP from interfering with the diameter changing points of the other internal components even when the insertion portion 5 is bent.

The coupling portion CP is disposed in such a position, thereby capable of preventing the coupling portion CP from contacting the other internal components and interfering with the movements of the other internal components, which results in an improvement of durability of the endoscope 2.

Furthermore, there is a case where internal structures of the operation portion and the like differ depending on types of endoscopes, even if the insertion lengths of the endoscopes are the same. There are various types of endoscopes including: a type having a rigidity varying mechanism of the insertion portion 5 in the operation portion 6, a type in which the shape of the operation portions 6 is different, a type in which the length of the bending portions 12 is different, a type in which the number of the channels in the insertion portion 5 is different, and the like, for example. Therefore, there is a case where the range of the region R1 in which the above-described channel tube 26 is completely unbendable and the region R2 in which the channel tube 26 is hardly bendable is different in the operation portion 6, for example.

Accordingly, the channel tube has been produced for each type of the endoscopes. Since the coil is wound around the channel tube, if the coil end is positioned in the bending range in the flexible tube, there is a possibility that the resin tube is buckled at the position of the coil end. Therefore, the channel tube is produced such that the position of the coil end is located within the range of the completely unbendable region (rigid portion) R1 and the hardly bendable region (quasi-rigid portion) R2. In contrast, the channel tube 26 according to the present embodiment can be produced by connecting the above-described two tubes and processing the channel tube into a desired length. Therefore, even when the range of the completely unbendable region (rigid portion) R1 and the hardly bendable region (quasi-rigid portion) R2 differs depending on the type of the endoscope 2, the coil end can be positioned in the region of the rigid portion R1 and the quasi-rigid portion R2 which is common to a plurality of types of endoscopes. Accordingly, it is possible to easily produce various channel tubes 26 suitable for several types of endoscopes without unnecessarily increasing the kinds of components.

Figure 10:
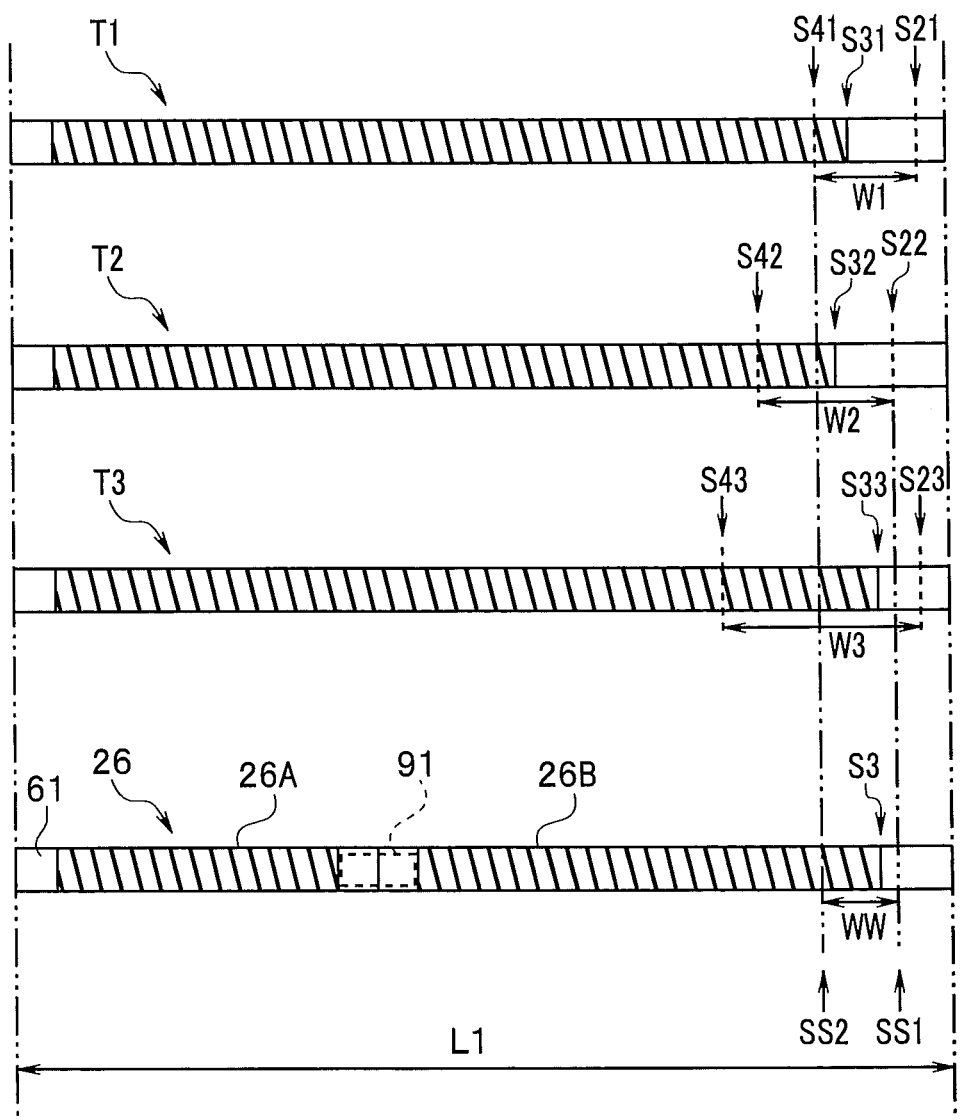
FIG. 10 relates to the first embodiment and illustrates that a range of a completely unbendable region (rigid portion) R1 and a hardly bendable region (quasi-rigid portion) R2 differs for each of a plurality of endoscopes.

FIG. 10 illustrates that the range of the completely unbendable region (rigid portion) R1 and the hardly bendable region (quasi-rigid portion) R2 differs for each of a plurality of endoscopes. FIG. 10 illustrates conventional three different types of channel tubes T1, T2, and T3 as examples, and the channel tube 26 formed by connecting the two tubes according to the present embodiment.

In the case of the channel tube T1, a position S31 of the coil end has only to be located within a range W1 from a position S21 at which the proximal end portion of the channel tube T1 is fixed to the position S41 of the distal end portion of the region (quasi-rigid portion) R2 in which the channel tube T1 is hardly bendable, in the endoscope in which the channel tube T1 is inserted.

In the case of the channel tube T2, a position S32 of the coil end has only to be positioned within a range W2 from a position S22 at which the proximal end portion of the channel tube T2 is fixed to a position S42 of the distal end portion of the region (quasi-rigid portion) R2 in which the channel tube T2 is hardly bendable, in the endoscope in which the channel tube T2 is inserted.

In the case of the channel tube T3, a position S33 of the coil end has only to be positioned within a range W3 from a position S23 at which the proximal end portion of the channel tube T3 is fixed to a position S43 of the distal end portion of the region (quasi-rigid portion) R2 in which the channel tube T3 is hardly bendable, in the endoscope in which the channel tube T3 is inserted.

Therefore, these three tubes have been conventionally produced for the respective types of endoscopes such that the respective positions of the coil ends are within the allowable ranges.

In contrast, the channel tube 26 according to the present embodiment can be produced by processing the length of the tube with high accuracy. Therefore, it is possible to produce the channel tube 26 by processing the tube such that the coil end is located within a range WW which is common to the ranges W1, W2, and W3.

Therefore, according to the present embodiment, as shown in FIG. 10, it is possible to produce the channel tube 26 such that, in the three tubes T1, T2 and T3, the position S3 of the coil end is positioned in the range WW which is common in the respective ranges from the positions at which the respective proximal end portions of the channel tubes are fixed to the positions of the distal end portions of the respective regions (quasi-rigid portions) R2 in which the respective channel tubes are hardly bendable. As a result, it is possible to produce a channel tube which can be commonly used for a plurality types of endoscopes, each of which has the same insertion lengths but has different structures. Therefore, the channel tube according to the present embodiment contributes to reduction in the production cost.

Note that, in the above-described embodiment, the front side tube 26A and the rear side tube 26B configuring the channel tube 26 are provided in the insertion portion 2 such that the front side tube 26A is disposed at a position on the distal end portion 11 side of the insertion portion 5 and the rear side tube 26B is disposed at a position on the operation portion 6 side. However, the front side tube 26A and the rear side tube 26B may be provided in the insertion portion 2 such that the positional relationship between the front side tube 26A and the rear side tube 26B is reversed. That is, the channel tube 26 may be provided in the insertion portion 2 such that the distal end side of the above-described front side tube 26A is disposed at a position on the operation portion 6 side and the proximal end side of the rear side tube 26B is disposed at a position on the distal end portion 11 side.

Moreover, the resin tube described in the above-described embodiment can be used not only for the channel tube as the above-described treatment instrument insertion channel inserted into the insertion portion as a flexible tube, but also for other tubes to be inserted into the insertion portion, such as a forceps raising stand wire protection tube.

As described above, according to the present embodiment, it is possible to provide the resin tube configured to be inserted in the flexible tube of the endoscope, the resin tube being able to be easily produced by being processed into a desired length, and being configured such that the coil end of the coil wound around the resin tube can be easily located at a desired position or within a desired range.

Second Embodiment

The first embodiment relates to the resin tube arranged in the insertion portion of the endoscope. The second embodiment relates to a resin tube arranged in the universal cord of the endoscope.

The universal cord for connecting the endoscope and other apparatuses is also a tube having flexibility and includes a resin tube such as a suction channel inserted therethrough. Therefore, also such a resin tube inserted through the universal cord can be configured by the resin tube formed by connecting two tubes as described in the first embodiment. Note that, in the present embodiment, the same constituent elements as those in the first embodiment are attached with the same reference numerals and description thereof will be omitted.

Figure 11:
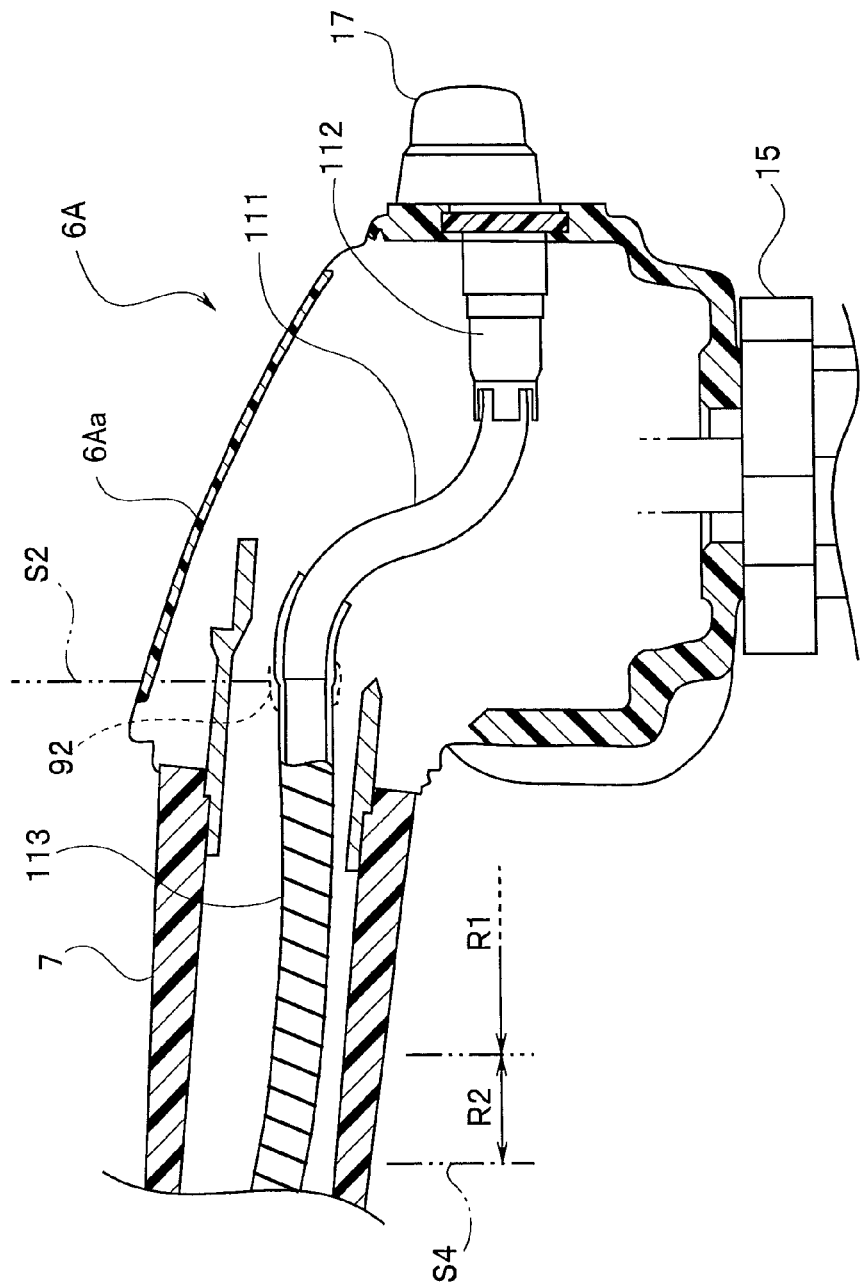
FIG. 11 relates to a second embodiment of the present invention, and illustrates an internal configuration of an operation portion 6 to which one end of a universal cable 7 is connected.

FIG. 11 illustrates an internal configuration of an operation portion 6A to which one end of the universal cord 7 is connected. FIG. 11 illustrates only the members related to the configuration of the resin tube in the operation portion 6A.

An S-shaped cylinder (hereinafter referred to as S-cylinder) 111 is provided in the exterior member 6Aa of the operation portion 6A, and fixed thereto by a fixing member, not shown. One end of the S-cylinder 111 is connected to a suction button 17 which is one of the operation buttons, through a connecting connector 112, and the other end of the S-cylinder is connected to one end of a suction channel tube 113 as the resin tube.

The suction channel tube 113 has the same configuration as that of the channel tube 26 described in the first embodiment, and configured by connecting the front side tube 26A and the rear side tube 26B with the connecting pipe 91. That is, the suction channel tube 113 is the resin tube inserted in the universal cord 7 as a flexible tube of the endoscope 2. The distal end portion of the front side tube 26A or the proximal end portion of the rear side tube 26B is connected to the S-cylinder 111.

Figure 12:
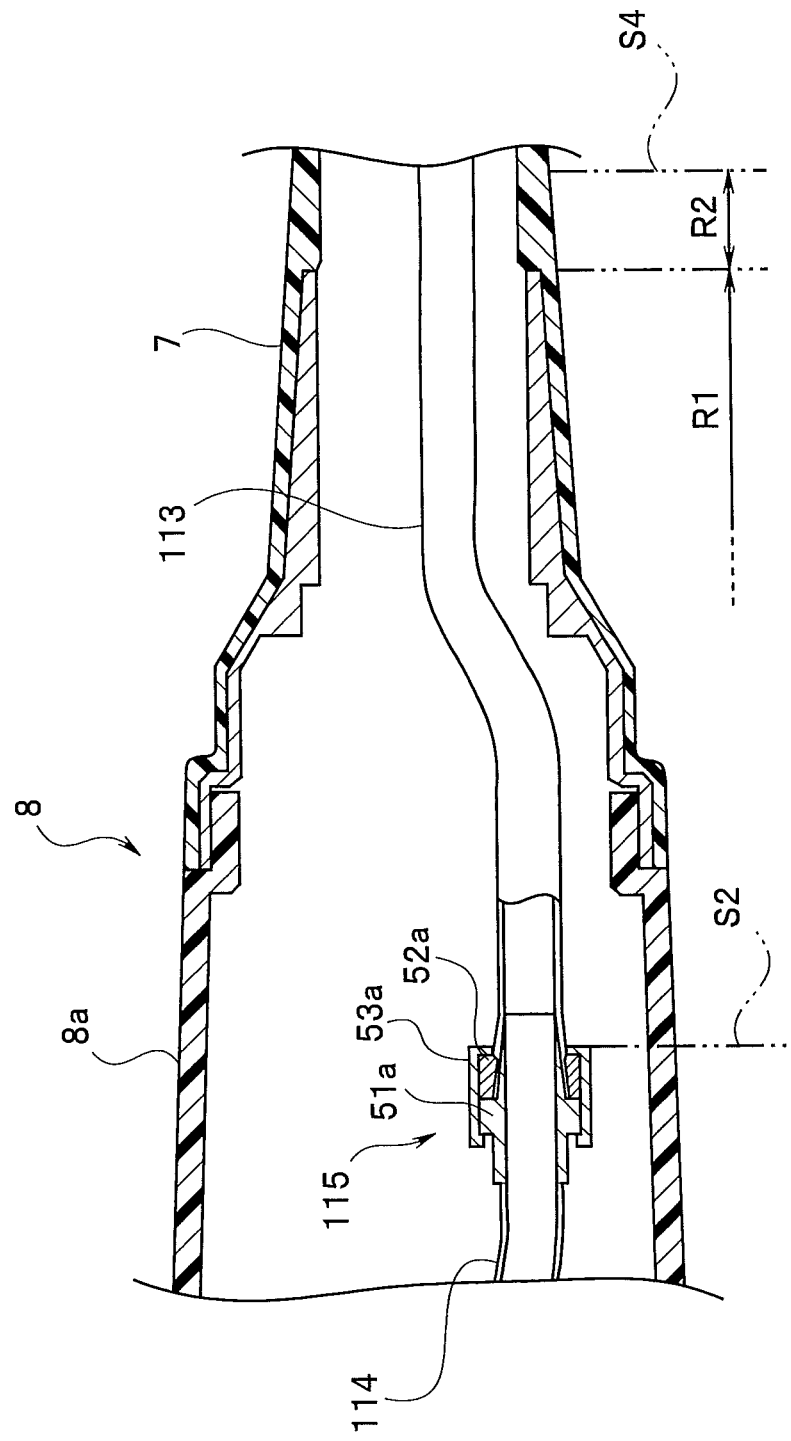
FIG. 12 relates to the second embodiment of the present invention, and illustrates an internal configuration of a light guide connector 8 provided at the other end of the universal cable 7.

FIG. 12 illustrates the internal configuration of the light guide connector 8 located at the other end of the universal cord 7. FIG. 12 only illustrates members related to the configuration of the resin tube in the light guide connector 8.

Inside an exterior member 8a of the light guide connector 8, a connection portion 115 for connecting the suction channel tube 113 and a tube 114 connected to a suction pump (not shown) in the light source device 3 is provided. The connection portion 115 is configured by the connecting member 51a, the tapered tube 52a, and the clamp nut 53a. A screw portion screwed with the screw portion of the clamp nut 53a is formed at a part of the outer circumference of the connecting member 51a. The connection portion 115 has a similar mechanism as that of the connecting member 51, the tapered tube 52 and the clamp nut 53 which are described in the first embodiment. Therefore, the clamp nut 53a is rotated and loosened, and it is possible to connect and fix the other end of the suction channel tube 113 to the gap between the connecting member 51a and the tapered tube 52a.

As described above, the suction channel tube 113 has the same configuration as that of the channel tube 26 described in the first embodiment. Therefore, the proximal end portion of the rear side tube 26B or the distal end portion of the front side tube 26A is connected to the connecting portion 115.

As shown in FIGS. 11 and 12, also the operation portion 6A and the light guide connector 8 include a region (rigid portion) R1 in which the suction channel tube 113 as the resin tube is completely unbendable, and a region (quasi-rigid portion) R2 in which the suction channel tube 113 is hardly bendable.

Therefore, it is possible to produce the suction channel tube 113 by processing the suction channel tube 113 such that the coil end of the rear side tube 26B is located within the range of the region (rigid portion) R1 in which the suction channel tube 113 is completely unbendable and the region (quasi-rigid portion) R2 in which the suction channel tube 113 is hardly bendable.

As described above, according to the present embodiment, it is possible to provide the resin tube configured to be inserted in the flexible tube of the endoscope, the resin tube being able to be easily produced by being processed into a desired length, and being configured such that the coil end of the coil wound around the resin tube can be easily located at a desired position or within a desired range.

Note that the resin tube in the universal cord may be configured by one of the front side tube 26A and the rear side tube 26B.

For example, the proximal end portion of the rear side tube 26B is fixed to the connecting portion 115 inside the light guide connector 8, and the distal end portion of the rear side tube 26B is fixed to the S-cylinder 111 of the operation portion 6A. At this time, the distal end portion of the rear side tube 26B is mounted to the S-cylinder 111 so as to be externally fitted thereon. Therefore, a part of the coil 34B, which is located from the distal end portion of the rear side tube 26B to the reference position S2 of the S-cylinder 111, is peeled and removed. Then, as shown by the dotted lines in FIG. 11, the resin material 92 is applied to the coil end portion for reinforcement.

Accordingly, one front side tube 26A or one rear side tube 26B is formed into a desired length using a jig, and the coil end located in a desired range is removed, thereby capable of producing the resin tube which has a desired length and which is configured such that the coil end is located at a desired position or within a desired range.

Further, there is a case where the inside of the above-described suction channel tube is cleaned with a cleaning brush. When the inside of the suction channel tube is cleaned with the cleaning brush, there is a possibility that the suction channel tube is holed by the inner wall surface of the suction channel tube being pressed and scraped with the cleaning brush. Therefore, in order to prevent a hole from being generated on the suction channel tube at the time of cleaning the suction channel tube with the cleaning brush, the following configuration is preferable.

Hereinafter, description will be made on a first to third methods for preventing generation of a hole caused by the cleaning brush.

Figure 13:
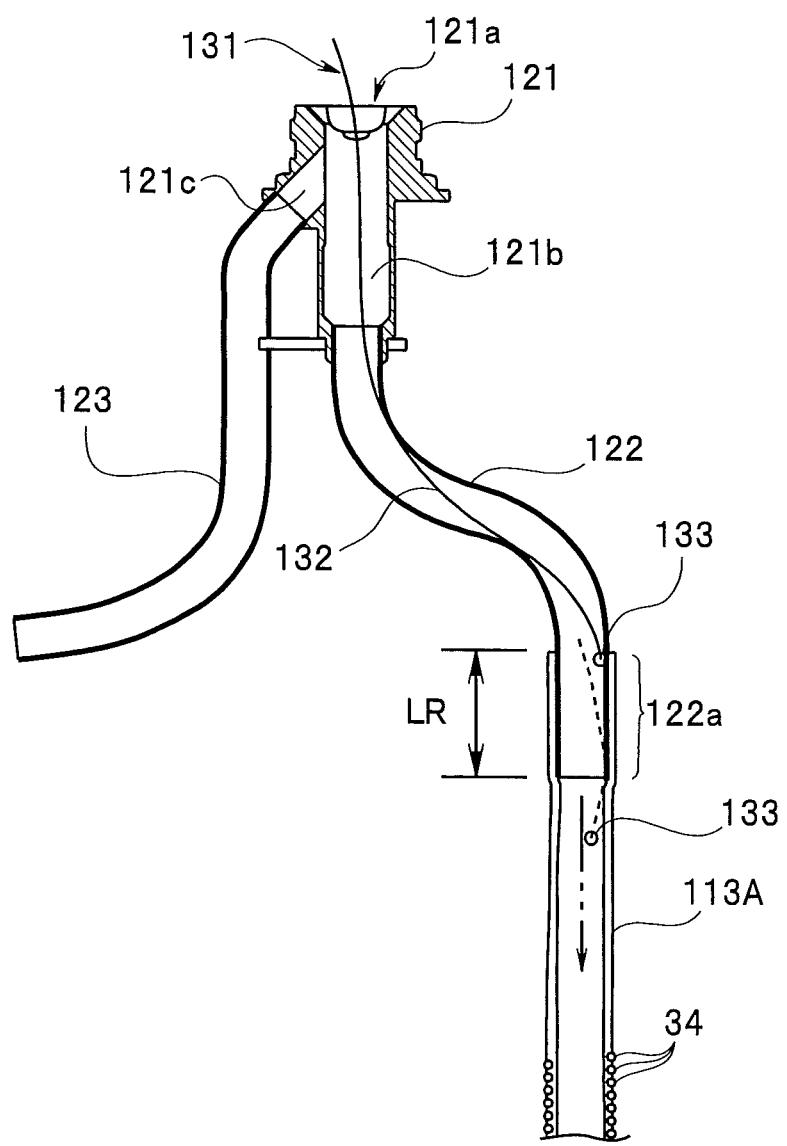
FIG. 13 relates to the second embodiment of the present invention, and illustrates a first method of preventing generation of a hole caused by a cleaning brush.

FIG. 13 illustrates a first method of preventing generation of a hole caused by the cleaning brush. FIG. 13 is a partial cross-sectional view for describing a connecting configuration between an S-cylinder 122 connected to a suction cylinder member 121 provided in the operation portion 6 and a suction channel tube 113A connected to the S-cylinder 122.

The suction cylinder member 121 as a connector is fixed to the exterior member of the operation portion 6. As shown in FIG. 13, the suction cylinder 121 includes one opening portion 121a, and two communicating holes 121b, 121c communicating with the opening portion 121a.

One end of the S-cylinder 122 is inserted in and connected to a proximal end side opening portion of the communicating hole 121b. One end of an S-cylinder 123 is inserted and connected to a proximal end side opening portion of the communicating hole 121c.

A straight portion 122a extended straight is formed on the other end of the S-cylinder 122, and one end of the suction channel tube 113A inserted into the universal cord 7 is externally fitted to the straight portion 122a. The other end of the S-cylinder 123 is connected to a connector (not shown) communicating with the treatment instrument insertion channel 23. The suction cylinder member 121, and the S-cylinders 122, 123 are made of metal, for example, a stainless steel.

The straight portion 122a of the S-cylinder 122 is connected with the one end of the front side tube 26A or the one end of the rear side tube 26B. The other end of the suction channel tube 113A inserted in the universal cord 7 is connected to a suction pump, not shown, through the connector portion on the light source device 3 side.

After the use of the endoscope, the cleaning brush 131 is inserted from the opening portion 121a in order to clean the inside of the S-cylinder 122 and the inside of the suction channel tube 113A. The cleaning brush 131 includes a shaft portion 132 which is formed by twisting a plurality of thin wire rods made of metal and which has flexibility, and a spherical portion 133 provided at the distal end portion of the shaft portion 132, and a brush portion (not shown) provided on the proximal end side of the spherical portion 133.

When the cleaning brush 131 is inserted from the opening portion 121a and pushed into the S-cylinder and the suction channel tube, since the cleaning brush 131 has flexibility, the cleaning brush 131 advances inside of the S-cylinder 122 and the suction channel tube 113A with the spherical portion 133 at the distal end and the shaft portion 132 contacting the inner surface of the S-cylinder 122 and the inner surface of the suction channel tube 113A.

As shown in FIG. 13, when the cleaning brush 131 passes through the S-cylinder 122, the distal end portion of the cleaning brush 131 and the distal end portion of the shaft portion 132 in the vicinity of the distal end portion of the cleaning brush contact the inner circumferential surface of the S-cylinder 122. Furthermore, also immediately after the distal end portion of the cleaning brush 131 passed through the S-shape portion of the S-cylinder 122, the distal end portion of the cleaning brush 131 does not advance straight along the axis direction of the suction channel tube 113A, but advances while maintaining an angle with respect to the axis direction of the suction channel tube 113A.

As shown in FIG. 13, the S-cylinder 122 includes the straight portion 122a connected to the suction channel tube 113A. The straight portion 122a has a length equivalent to the length of the region LR within which the distal end portion of the cleaning brush 131 advances while maintaining an angle with respect to the axis direction of the suction channel tube 113A, immediately after the distal end portion of the cleaning brush 131 passed through the S-shaped portion of the S-cylinder 122. FIG. 13 illustrates the state where the distal end portion of the cleaning brush 131 contacts the inner surface of the straight portion 122a, and the state where the bent shaft portion 132 contacts the inner surface of the straight portion 122a, as shown by the dotted line.

Since the straight portion 122a of the rigid S-cylinder 122 made of metal or the like is located in the range LR, a hole is not generated or a hole is hardly generated at the part with which the distal end portion of the cleaning brush 131 and the distal end portion of the shaft portion 132 in the vicinity of the distal end portion of the cleaning brush 131 are brought into contact. If the suction channel tube 113A is located in the range LR, the suction channel tube is pressed by the distal end portion of the cleaning brush 131 and the bent portion of the shaft portion 132 in the vicinity of the distal end portion of the cleaning brush, and the inner wall of the suction channel tube 113A is scraped, for example, which possibly causes generation of a hole on the inner wall.

In addition, also when the inserted cleaning brush 131 is extracted, the distal end portion of the cleaning brush 131 and the bent portion of the shaft portion 132 in the vicinity of the distal end portion of the cleaning brush similarly contact the straight portion 122a of the S-cylinder 122 in the range LR. Therefore, the inner wall of the straight portion 122a is not scraped, thereby preventing generation of a hole, for example.

When the distal end portion of the cleaning brush 131 passes through the range LR within which the distal end portion of the cleaning brush 131 advances while maintaining an angle with respect to the axis direction of the suction channel tube 113A, the distal end portion of the cleaning brush 131 advances straight along the axis direction of the suction channel tube 113A, as shown by the arrow of the two-dot-chain line in FIG. 13.

As described above, the S-cylinder 122 connected to the suction cylinder member 121 includes the straight portion 122a which is formed to be straight, in the range LR which is a part connected to the suction channel tube 113A and in which the distal end portion of the cleaning brush 131 advances while maintaining an angle with respect to the axis direction of the suction channel tube 113A. Therefore, when inserting and extracting the cleaning brush 131, it is unlikely that a hole is generated by the cleaning brush 131 at the connecting part between the S-cylinder 122 and the suction channel tube 113A.

Figure 14:
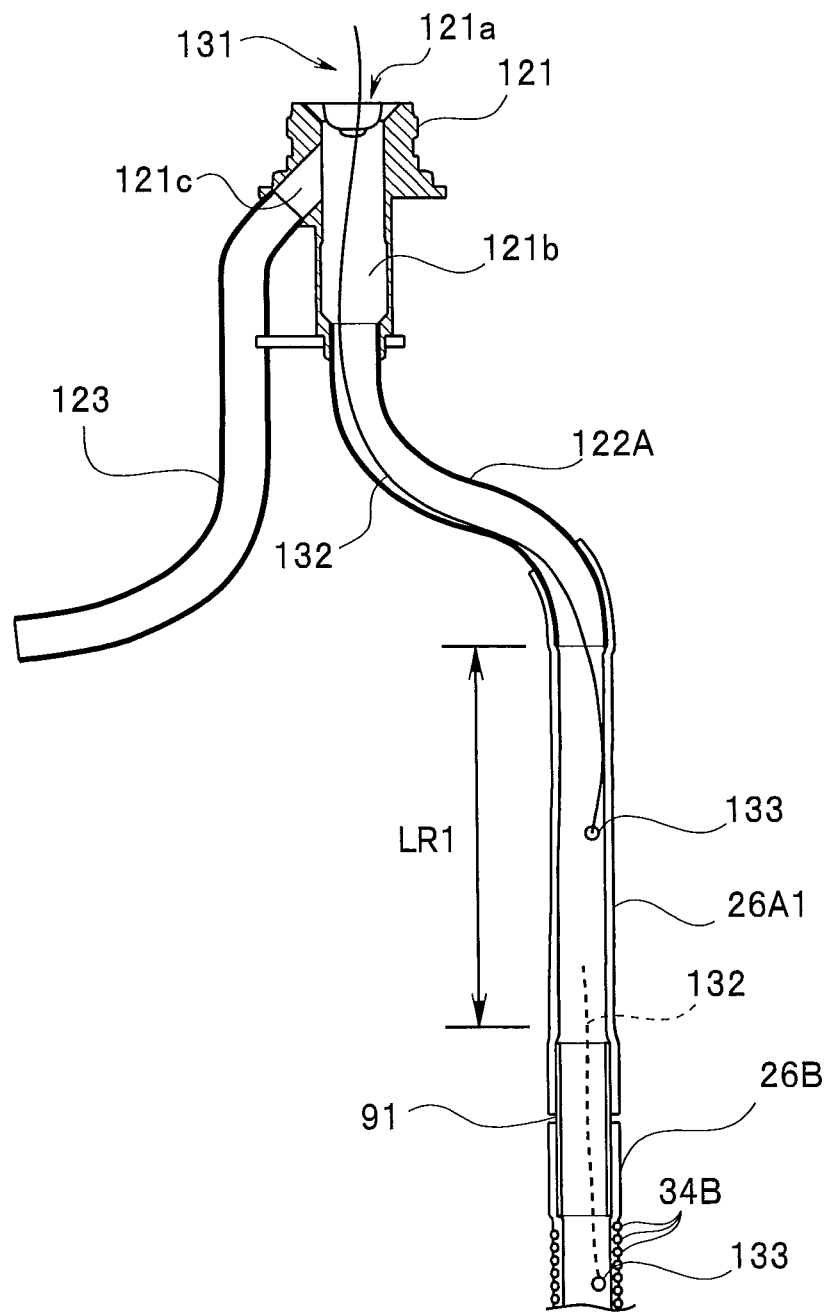
FIG. 14 relates to the second embodiment of the present invention, and illustrates a second method of preventing generation of a hole caused by the cleaning brush.

FIG. 14 illustrates a second method of preventing generation of a hole caused by the cleaning brush. In FIG. 14, the same constituent elements as those in FIG. 13 are attached with the same reference numerals and description thereof will be omitted.

As shown in FIG. 14, the S-cylinder 122A connected to the suction cylinder member 121 does not have the straight portion 122a shown in FIG. 13. One end of the S-cylinder 122A is connected with the suction channel tube 113A, and in this case, connected with one end of a front side tube 26A1. The front side tube 26A1 is connected to the rear side tube 26B with the connecting member 91.

The front side tube 26A1 in FIG. 14 is a Teflon (registered trademark) tube, for example, and has a thin-wall portion which is thicker than a thin-wall portion of the rear side tube 26B. Furthermore, the coil 34A is not wound around the front side tube 26A1. Note that, in FIG. 14, a range of LR1 in which the distal end portion of the cleaning brush 131 advances while maintaining an angle with respect to the axis direction of the suction channel tube 113A, immediately after the distal end portion of the cleaning brush 131 passed through the S-shaped portion of the S-cylinder 122A is illustrated to be longer than the range LR in FIG. 13.

The range LR1 of the front side tube 26A1 is a range in which the cleaning brush 131 strongly presses the inner surface of the suction channel tube 113A, and the cleaning brush 131 is not strongly pressed against the inner surface of the rear side tube 26B.

Therefore, since the thick front side tube 26A1 is located in the range LR1, when the cleaning brush 131 is inserted and extracted, a hole is hardly generated by the cleaning brush 131 at the connecting part between the S-cylinder 122A and the resin tube 26A1 and a part in the vicinity of the connecting part.

Figure 15:
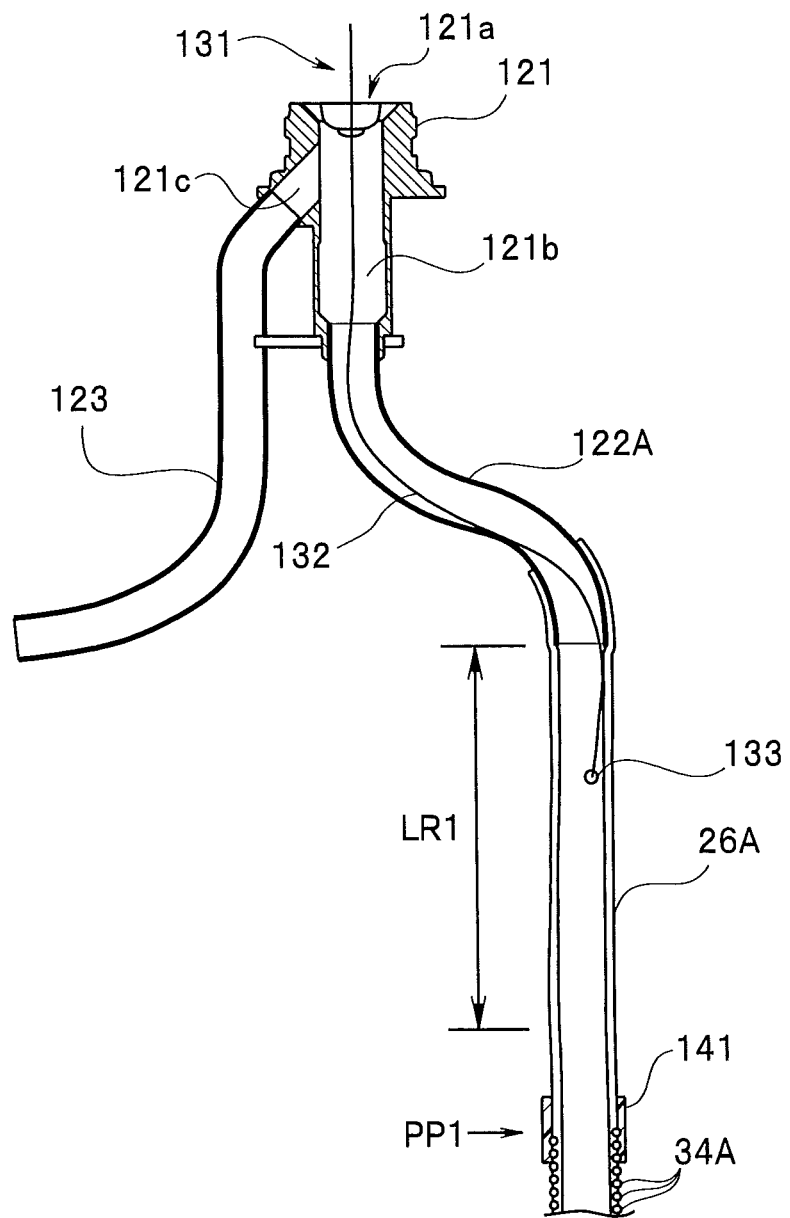
FIG. 15 relates to the second embodiment of the present invention, and illustrates a third method of preventing generation of a hole caused by the cleaning brush.

FIG. 15 illustrates a third method of preventing generation of a hole caused by the cleaning brush. In FIG. 15, the same constituent elements as those in FIGS. 13 and 14 are attached with same reference numerals and description thereof will be omitted.

As shown in FIG. 15, the one end of the S-cylinder 122A connected to the suction cylinder member 121 is connected with the suction channel tube 113A, and in this case, connected with one end of the front side tube 26A.

The coil 34A is wound around the front side tube 26A in FIG. 15. The coil end of the coil 34A is fixed to the front side tube 26A using a heat-shrinkable tube 141. If an adhesive or the like is used for fixing the coil end, curing time and applying operation of the adhesive are required. However, if the heat-shrinkable tube 141 is used, these time and operation are not required, thereby improving workability.

The coil 34A is formed such that a position PP1 of the coil end of the coil 34A wound around the front side tube 26A is located closer to the connector side of the light source device 3 than the range LR1 in which the distal end portion of the cleaning brush 131 advances while maintaining an angle with respect to the axis direction of the suction channel tube 113A.

On the surface of the front side tube 26A, thickness of the thin-wall portion at the part where the coil 34A is not wound is greater than the thin-wall portion of the part where the coil 34A is wound, since the groove 81A is not formed.

In the range LR1, the thick part of the front side tube 26A is located. Therefore, when the cleaning brush 131 is inserted and extracted, a hole is hardly generated by the cleaning brush 131 at the connecting part between the S-cylinder 122A and the resin tube 26A.

Note that the resin tube inserted in the universal cord as the flexible tube described in the above-described present embodiment can be applied not only to the above-described suction channel tube but also to other tubes such as an air/water feeding tube and an auxiliary water feeding tube.

As described above, according to the above-described first and second embodiments, it is possible to provide the resin tube configured to be inserted in the flexible tube of the endoscope or the universal cord, the resin tube being able to be easily produced by being processed into a desired length, and being configured to allow the coil end of the coil wound around the resin tube to be located at a desired position or within a desired range, thereby enabling various channel tubes respectively corresponding to a plurality of types of endoscopes to be easily produced without increasing the number of components.

The present invention is not limited to the above-described embodiments but various changes and modifications are possible without departing from the gist of the present invention.

What is claimed is:

1. A resin tube configured to be inserted in a flexible tube of an endoscope or a connection cable, the resin tube comprising:
   a first resin tube including, on a part of an outer surface thereof, a helical-shaped first groove;
   a second resin tube including, on a part of an outer surface thereof, a helical-shaped second groove;
   a first coil wound on the first groove of the first resin tube;
   a second coil wound on the second groove of the second resin tube; and
   a connecting pipe configured to connect one end of the first resin tube and one end of the second resin tube,
   wherein the first resin tube is externally fitted and connected to the connecting pipe at a coil-removed part where the first groove is formed and the first coil is peeled, removed and not wound, and
   the second resin tube is externally fitted and connected to the connecting pipe at a part where the second coil is not wound.

2. The resin tube according to claim 1, wherein the second resin tube is connected to the connecting pipe at a part where the second groove is not formed and the second coil is not wound.

3. The resin tube according to claim 2, wherein a depth of the first groove of the first resin tube is smaller than a diameter of a first wire configuring the first coil and larger than a radius of the first wire, and a depth of the second groove of the second resin tube is smaller than a diameter of a second wire configuring the second coil and larger than a radius of the second wire.

4. The resin tube according to claim 1, wherein an end portion of the first coil wound around the first resin tube is covered with resin, the end portion being located on a side of the connecting pipe.

5. The resin tube according to claim 1, wherein a surface of at least one of the first resin tube and the second resin tube is subjected to a coating.

6. The resin tube according to claim 5, wherein, when both of a surface of the first resin tube and a surface of the second resin tube are subjected to the coating, the first resin tube and the second resin tube differ from each other in at least one of thicknesses of coating materials applied to the first resin tube and the second resin tube, kinds of the coating materials, and ranges to which the coating materials are applied.

7. The resin tube according to claim 1, wherein the first coil wound around the first resin tube and the second coil wound around the second resin tube differ from each other in at least one of rigidity or elasticity.

8. The resin tube according to claim 1, wherein the first resin tube and the second resin tube differ from each other in at least one of: diameters of the first wire configuring the first coil and the second wire configuring the second coil; materials of the first wire configuring the first coil and the second wire configuring the second coil; helical pitches of the first coil and the second coil; and the depths of the first groove and the second groove.

9. The resin tube according to claim 1, wherein at least one of a first wire configuring the first coil and a second wire configuring the second coil has spring property.

10. The resin tube according to claim 1, wherein the resin tube is a channel tube for treatment instrument insertion channel, or a forceps raising stand wire protection tube.

11. The resin tube according to claim 1, wherein the resin tube is a suction channel tube, an air/water feeding tube, or an auxiliary water feeding tube.

12. An endoscope comprising:
  an insertion portion including a flexible tube configured to be inserted into an observation target;
  an operation portion provided in a linked manner on a proximal end side of the insertion portion;
  a connection cable configured to connect the operation portion and other devices; and
  a resin tube configured to be inserted into the flexible tube or the connection cable, the resin tube including:
    a first resin tube including, on a part of an outer surface thereof, a helical-shaped first groove;
    a second resin tube including, on a part of an outer surface thereof, a helical-shaped second groove;
    a first coil wound on the first groove of the first resin tube;
    a second coil wound on the second groove of the second resin tube; and
    a connecting pipe configured to connect one end of the first resin tube and one end of the second resin tube,
    wherein the first resin tube is externally fitted and connected to the connecting pipe at a part where the first groove is formed and
    at a coil-removed region where the first coil is peeled, removed and not wound, and the second resin tube is externally fitted and connected to the connecting pipe at a part where the second coil is not wound.

13. The endoscope according to claim 12, wherein the first resin tube is disposed on a rear end side of the flexible tube of the endoscope, and the second resin tube is disposed on a distal end side of the flexible tube of the endoscope.

14. The endoscope according to claim 12, wherein the first resin tube is disposed on a distal end side of the flexible tube of the endoscope, and the second resin tube is disposed on a rear end side of the flexible tube of the endoscope.

* * * * *